(12) United States Patent
Luo

(10) Patent No.: US 11,485,905 B2
(45) Date of Patent: Nov. 1, 2022

(54) GREEN LIGHT THERMALLY ACTIVATED DELAYED FLUORESCENT MATERIAL AND SYNTHESIZING METHOD THEREOF, AND ELECTROLUMINESCENT DEVICE

(71) Applicant: Wuhan China Star Optoelectronics Semiconductor Display Technology Co., Ltd., Wuhan (CN)

(72) Inventor: Jiajia Luo, Wuhan (CN)

(73) Assignee: Wuhan China Star Optoelectronics Semiconductor Display Technology Co., Ltd., Wuhan (CN)

(*) Notice: Subject to any disclaimer, the term of this patent is extended or adjusted under 35 U.S.C. 154(b) by 634 days.

(21) Appl. No.: 16/326,206

(22) PCT Filed: Dec. 29, 2018

(86) PCT No.: PCT/CN2018/125352
§ 371 (c)(1),
(2) Date: Feb. 17, 2019

(87) PCT Pub. No.: WO2020/098114
PCT Pub. Date: May 22, 2020

(65) Prior Publication Data
US 2020/0224088 A1     Jul. 16, 2020

(30) Foreign Application Priority Data
Nov. 15, 2018  (CN) .......................... 201811359848.8

(51) Int. Cl.
*C09K 11/06*       (2006.01)
*C07D 265/38*   (2006.01)
(Continued)

(52) U.S. Cl.
CPC ............ *C09K 11/06* (2013.01); *C07D 265/38* (2013.01); *C07D 413/04* (2013.01);
(Continued)

(58) Field of Classification Search
None
See application file for complete search history.

(56) References Cited

U.S. PATENT DOCUMENTS

2019/0027693 A1    1/2019  Zysman-Colman et al.

FOREIGN PATENT DOCUMENTS

| CN | 102449109 | 5/2012 |
| CN | 106083824 | 11/2016 |

(Continued)

OTHER PUBLICATIONS

Fors et al. (J. Am. Chem. Soc. 2010, 132, 15914-15917).*
El-Deeb et al. (Molecules 2008, 13, 818-830).*
Poole (III/Flash Chromatography 2000, 2808-2814).*

*Primary Examiner* — Jay Yang

(57) ABSTRACT

A green light thermally activated delayed fluorescent material and a synthesizing method thereof, and an electroluminescent device are described. The green light thermally activated delayed fluorescent material is a target compound reacted and synthesized by an electron donor and an electron acceptor. The target compound is a D-A molecular structure. The electron acceptor has a fluorine-containing group and a bromine-containing group. The electron acceptor is a planar electron acceptor with an ultra-low triplet state energy level, and a triplet state energy level of the target compound ranges from 1.0 to 2.0 eV. The synthesized green light thermally activated delayed fluorescent material improves a luminous efficiency and realizes a preparation of a high efficiency organic electroluminescent device.

8 Claims, 2 Drawing Sheets

(51) Int. Cl.
*C07D 413/04* (2006.01)
*H01L 51/00* (2006.01)
*H01L 51/50* (2006.01)
*H01L 51/56* (2006.01)

(52) U.S. Cl.
CPC ...... *H01L 51/0071* (2013.01); *H01L 51/0072* (2013.01); *C09K 2211/1011* (2013.01); *C09K 2211/1018* (2013.01); *H01L 51/001* (2013.01); *H01L 51/5012* (2013.01); *H01L 51/56* (2013.01); *H01L 2251/558* (2013.01)

(56) References Cited

FOREIGN PATENT DOCUMENTS

| | | |
|---|---|---|
| CN | 108047228 | 5/2018 |
| CN | 108780852 | 11/2018 |
| CN | 109134347 | 1/2019 |
| WO | WO2017/115068 | 7/2017 |
| WO | WO-2017/115068 A1 * | 7/2017 |
| WO | WO-2017/115068 A1 * | 7/2017 |

* cited by examiner

GREEN LIGHT THERMALLY ACTIVATED DELAYED FLUORESCENT MATERIAL AND SYNTHESIZING METHOD THEREOF, AND ELECTROLUMINESCENT DEVICE

RELATED APPLICATIONS

This application is a National Phase of PCT Patent Application No. PCT/CN2018/125352 having International filing date of Dec. 29, 2018, which claims the benefit of priority of Chinese Patent Application No. 201811359848.8 filed on Nov. 15, 2018. The contents of the above applications are all incorporated by reference as if fully set forth herein in their entirety.

FIELD AND BACKGROUND OF THE INVENTION

The present disclosure relates to displays, and more particularly to a green light thermally activated delayed fluorescent material and a synthesizing method thereof, and an electroluminescent device.

At present, organic light-emitting diodes (OLEDs) have advantages of being active illumination without requiring backlight, high luminous efficiency, large viewing angle, fast response times, large temperature adaptation range, relatively simple production and processing technology, low driving voltage, low energy consumption, lighter and thinner, flexible display, etc., and a huge application prospects, so as to attract an attention of many researchers. In OLED, it is critical to have a light-emitting guest material play a leading role. A light-emitting guest material, used in early OLEDs, is a fluorescent material. Because of a 1:3 ratio of singlet state to triplet state excitons in the OLED, a theoretical internal quantum efficiency (IQE) of the OLED based on fluorescent materials can only reach 25%, which greatly limits application of fluorescent electroluminescent devices. Heavy metal complex phosphorescent materials can utilize singlet state and triplet state excitons simultaneously due to a spin-orbit coupling of heavy atoms, resulting in an internal quantum efficiency (IQE) of 100%. However, the heavy metals commonly used are precious metals such as Ir and Pt, and heavy metal complex phosphorescent materials in terms of blue light materials still need to be broken. Pure organic thermally activated delayed fluorescence (TADF) materials, through clever molecular design, allow molecules to have a relatively small minimum singlet-triplet level difference. Thus, the triplet state excitons can be returned to the singlet state by reverse intersystem crossing (RISC), and then illuminate by the radiation transition to the ground state, so that the singlet state and triplet state excitons can be simultaneously utilized, and the internal quantum efficiency (IQE) can achieve 100%.

For thermally activated delayed fluorescence materials, fast reverse intersystem crossing constants ($k_{RISC}$) and high photoluminescence quantum yields are necessary for a preparation of high efficiency OLEDs. At present, thermally activated delayed fluorescence materials with the above conditions are still relatively scarce compared to heavy metal Ir complexes.

SUMMARY OF THE INVENTION

An object of the present disclosure is to provide a green light thermally activated delayed fluorescence material and a synthesis method thereof and a synthesizing method thereof, and an electroluminescent device, and an electroluminescent device, so as to solve technical problems of low photoluminescence quantum yield in a conventional thermally activated delayed fluorescent material system and a low proportion of the thermally activated delayed fluorescent material in an entire thermally activated delayed fluorescent material system.

To achieve the above object, the present disclosure provides green light thermally activated delayed fluorescent material, which is a target compound reacted and synthesized by an electron donor and an electron acceptor, wherein the target compound is a D-A molecular structure, wherein, in the D-A molecular, the D is the electron donor, the A is the electron acceptor, the electron acceptor has a fluorine-containing group and a bromine-containing group, the electron acceptor is a planar electron acceptor with an ultra-low triplet state energy level, and a triplet state energy level of the target compound ranges from 1.0 to 2.0 eV.

Further, the electron donor is phenoxazine, and a molecular structure of the electron acceptor is one of

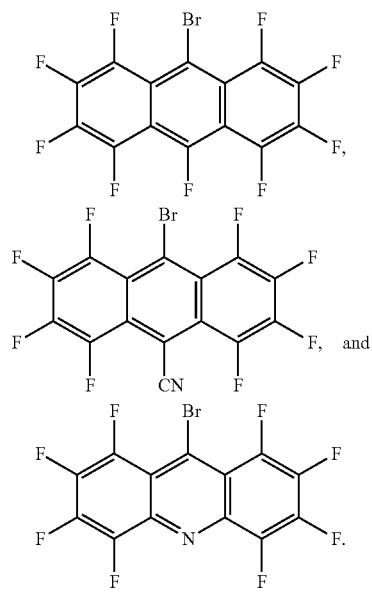

Further, the D-A molecular structure of the green light thermally activated delayed fluorescent material is one of

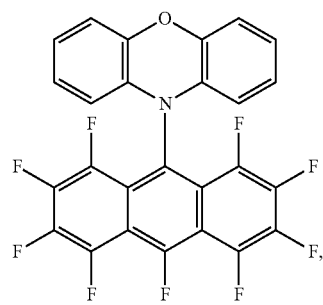

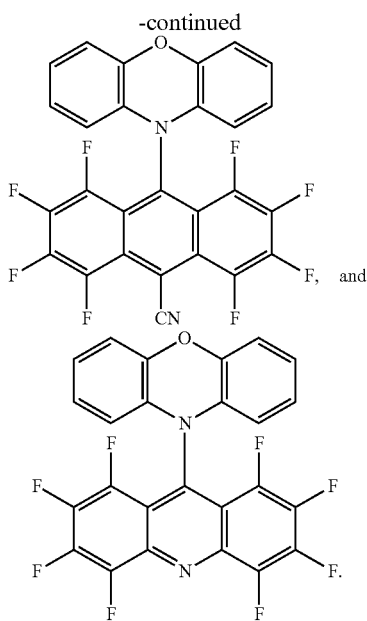

The present disclosure provides a synthesizing method of a green light thermally activated delayed fluorescent material, comprising following steps of: a reaction solution preparation step of placing an electron donor, an electron acceptor, and a catalyst into a reaction vessel to obtain a reaction solution; a target compound synthesis step of placing the reaction solution at a temperature from 110° C. to 130° C. to thoroughly react and thus obtain a mixed solution, wherein the mixed solution has a target compound formed after reacting; an extraction step of cooling the mixed solution to a room temperature to extract the target compound from the mixed solution; and a target compound purification treatment step of separating and purifying the target compound to obtain the green thermally activated delayed fluorescent material.

Further, the electron donor is phenoxazine, and a molecular structure of the electron acceptor is one of and the catalyst includes palladium acetate, tri-tert-butylphosphine tetrafluoroborate, and sodium t-butoxide.

Further, in the reaction solution preparation step, a molar ratio of the electron acceptor to the electron donor is from 1:1 to 1:3.

Further, in the reaction solution preparation step, the palladium acetate and the tri-tert-butylphosphine tetrafluoroborate together with the electron donor and the electron acceptor are firstly placed into the reaction vessel, the reaction vessel is further placed under an argon gas environment, and the sodium t-butoxide and toluene which removes water and oxygen are added into the reaction vessel, so as to obtain the reaction solution.

Further, the extraction step comprises: pouring the reaction solution into an ice water mixture, and performing multiple extractions using dichloromethane; and after the multiple extractions, combining organic phases to obtain the target compound.

Further, a step of purifying the target compound comprises: purifying the target compound by a silica gel column chromatography using a developing solvent to obtain a purified product, wherein the developing agent in the silica gel column chromatography method is dichloromethane and n-hexane, and a volume ratio of the dichloromethane to the n-hexane is 3:2.

The present disclosure further provides an electroluminescent device, comprising: a substrate layer; a hole injecting layer disposed on a side surface of the substrate layer; a transporting layer disposed on a side surface of the hole injecting layer away from the substrate layer; a luminescent layer disposed on a side surface of the transporting layer away from the hole injecting layer; an electron transporting layer disposed on a side surface of the luminescent layer away from the transporting layer; and a cathode layer disposed on a side surface of the electron transporting layer away from the luminescent layer; wherein a material of the luminescent layer is a green light thermally activated delayed fluorescent material.

A technical effect of the present disclosure is that the green light thermally activated delayed fluorescent material of the present disclosure use a clever molecular design to have a low singlet-triplet state energy level difference, a high luminous efficiency, and a fast reverse crossing enthalpy constant (a constant value ranging from $1*10^4$/s to $1*10^7$/s), and achieve a structure being fine-tuned to cover the spectrum from blue light to green light simultaneously.

The synthesizing method of the green light thermally activated delayed fluorescent material described by the present disclosure synthesizes a series of green light thermally activated delayed fluorescent material activated delayed fluorescent materials having significant thermal activation delayed fluorescence characteristics by a combination of different functional groups, wherein a synthesizing percentage is high. Among the synthesized product, the thermally activated delayed fluorescent material has a high proportion in the entire synthesized product, and its photoluminescence quantum yield is high.

The electroluminescent device of the present disclosure use a green light thermally activated delayed fluorescent material to fabricate a luminescent layer, such that the organic electroluminescent device having the green light thermally activated delayed fluorescent material has a relatively high luminous efficiency and brightness.

Figure 1:
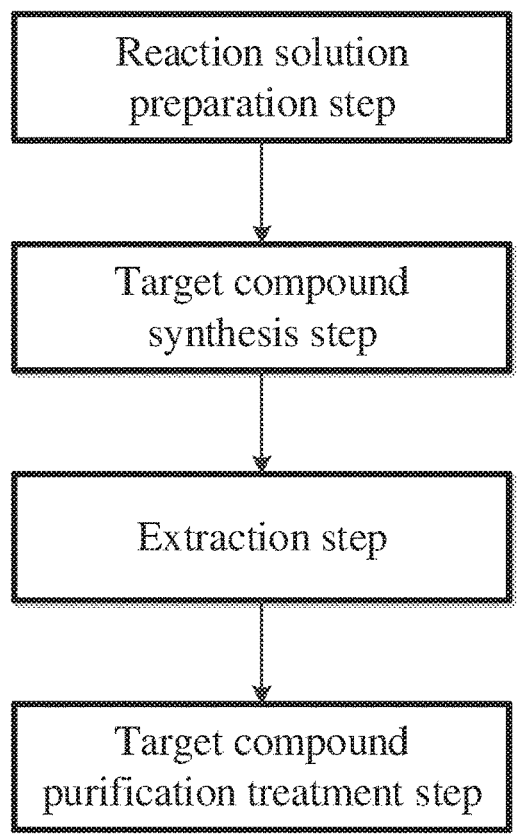
FIG. 1 is a flowchart of a synthesizing method of a green light thermally activated delayed fluorescent material according to an embodiment of the present disclosure.

Some components are identified as follows:

1: substrate layer;
2: hole injecting layer;
3: transporting layer
4: luminescent layer;
5: electron transporting layer;
6: cathode layer;
101: first curve;
102: second curve; and
103: third curve

DESCRIPTION OF SPECIFIC EMBODIMENTS OF THE INVENTION

Preferred embodiments of the present disclosure are described in detail below with reference to the accompanying drawings in order to explain technical details of the present disclosure to those skilled in the art so as to exemplify the disclosure. Those skilled in the art will more readily understand how to implement the disclosure. The present disclosure, however, may be embodied in many different forms of embodiments, and the scope of the present disclosure is not limited to the embodiments described herein. The description of the embodiments below is not intended to limit the scope of the disclosure.

The directional terms described by the present disclosure, such as "upper", "lower", "front", "back", "left", "right", "inner", "outer", "side", etc. are only directions by referring to the accompanying drawings. Thus, the used directional terms are used to describe and understand the present disclosure, but the scope of the present disclosure is not limited thereto.

In figures, elements with similar structures are indicated with the same numbers. Components that are structurally or functionally similar are denoted by similar reference numerals. Moreover, size and thickness of each component shown in the drawings are arbitrarily shown for ease of understanding and description, and the disclosure does not limit the size and thickness of each component.

When some components are described as "on" another component, the components may be placed directly on the another component; or may also be an intermediate component in which the component is placed on the intermediate component, and the intermediate component is placed on the another component.

Embodiment 1

The present embodiment provides a green light thermally activated delayed fluorescent material, which is a target compound reacted and synthesized by an electron donor and an electron acceptor, wherein the target compound is a D-A molecular structure, wherein, in the D-A molecular, the D is the electron donor, the A is the electron acceptor, the electron acceptor has a fluorine-containing group and a bromine-containing group, the electron acceptor is a planar electron acceptor with an ultra-low triplet state energy level, and a triplet state energy level of the target compound ranges from 1.0 to 2.0 eV. In the present embodiment, the electron donor is phenoxazine, and a molecular structure of the electron acceptor is

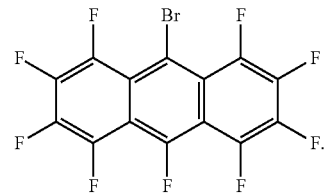 [SMILES: Fc1c(F)c(F)c2c(Br)c3c(F)c(F)c(F)c(F)c3c(F)c2c1F]

A molecular structure of a first target compound synthesized by the electron donor and the electron acceptor is as follows:

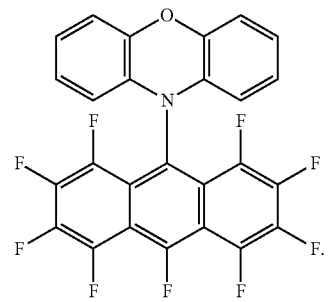 [SMILES: Fc1c(F)c(F)c2c(N3c4ccccc4Oc4ccccc43)c3c(F)c(F)c(F)c(F)c3c(F)c2c1F]

The present embodiment uses a clever molecular design to synthesize a green light thermally activated delayed fluorescent material having a low singlet-triplet state energy level difference, a high luminous efficiency, and a fast reverse crossing enthalpy constant (a constant value ranging from $1*10^4$/s to $1*10^7$/s), and achieve a structure being fine-tuned to cover the spectrum from blue light to green light simultaneously.

As shown in FIG. 1, in order to explain the green light thermally activated delayed fluorescent material of the present disclosure in more detail, the embodiment further provides a synthesizing method of the green light thermally activated delayed fluorescent material, which has a reaction formula substantially as shown in formula (1):

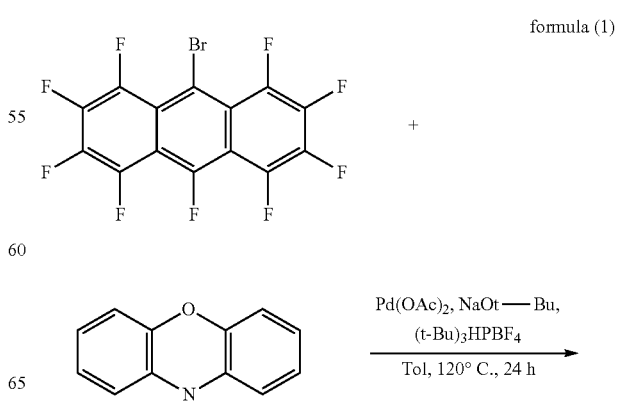

formula (1)

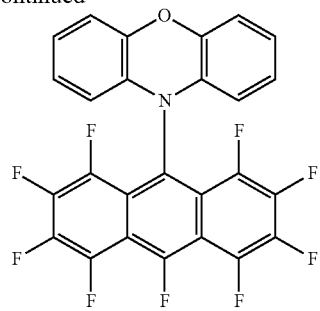

In formula (1), a molar ratio of the electron acceptor to the electron donor is from 1:1 to 1:3.

The synthesizing method of the present embodiment is explained in detail below with reference to formula (1), which includes the following steps:

In a reaction solution preparation step, 2.09 g (5 mmol) of the electron acceptor, 1.1 g (6 mmol) of the electron donor of phenoxazine, a catalyst of 45 mg (0.2 mmol) of palladium acetate, and 0.17 g (0.6 mmol) of tri-tert-butylphosphine tetrafluoroborate are placed in a 100 mL two-necked flask, and 0.58 g (6 mmol) of sodium t-butoxide (NaOt-Bu) is added into the 100 mL two-necked flask in a glove box, the reaction liquid is obtained. Because sodium t-butoxide (NaOt-Bu) reacts easily with water to release hydrogen, it is very dangerous. Therefore, it is stored in the glove box under an argon atmosphere, and it is also used under the argon atmosphere.

In a target compound synthesis step, reaction conditions of the reaction solution are provided. 30 mL to 50 mL of water-and-oxygen removed toluene are added into the glove box to thoroughly react at a temperature of 100° C. to 200° C. to obtain a mixed solution. The mixed solution has a first target compound formed by the reaction.

In an extraction step, the mixed solution is cooled to a room temperature and poured into a 100 mL to 300 mL ice-water mixture. The first target compound in the mixed solution is extracted multiple times with the dichloromethane.

In a target compound purification treatment step, an organic phase is combined, and the first target compound is initially purified by silica gel column chromatography using a developing solvent to obtain a purified product. In the silica gel column chromatography method, the developing agent is dichloromethane and n-hexane, and a volume ratio of the dichloromethane to n-hexane is 3:2. The first target compound is isolated and purified to obtain a blue white powder of 2.0 g in a yield of 77%.

Parameter analysis of the obtained first target compound is performed by a detecting instrument, and the analysis results include a nuclear magnetic resonance spectrum result, a carbon spectrum result, and a mass spectrometry result. Among them, results of a nuclear magnetic resonance spectrum and a carbon spectrum are $^1$H NMR (300 MHz, $CD_2Cl_2$, δ): 7.14 (t, J=6.3 Hz, 2H), 7.01-6.96 (m, 6H). A mass spectral results is: MS (EI) m/z: [M]+calcd (theoretical value) for $C_{26}H_8F_9NO$, 521.05; found (experimental value), 521.00.

The present embodiment synthesizes a green light thermally activated delayed fluorescent material having significant thermal activation delayed fluorescence characteristics by a combination of different functional groups, wherein a synthesizing percentage is high. In the synthesized product, the thermally activated delayed fluorescent material has a high proportion in the entire synthesized product, and its photoluminescence quantum yield is high.

Characteristic parameters of the first target compound are analyzed below, and the analysis results are shown in Table 1 below.

Table 1 shows the measured parameters such as the lowest singlet state (S1) and the lowest triplet state energy level (T1) of the first target compound:

| Compound | PL Peak (nm) | $S_1$ (eV) | $T_1$ (eV) | $\Delta E_{ST}$ (eV) | HOMO (eV) | LUMO (eV) |
| --- | --- | --- | --- | --- | --- | --- |
| First target compound | 464 | 2.67 | 2.60 | 0.07 | −5.52 | −2.43 |

Figure 2:
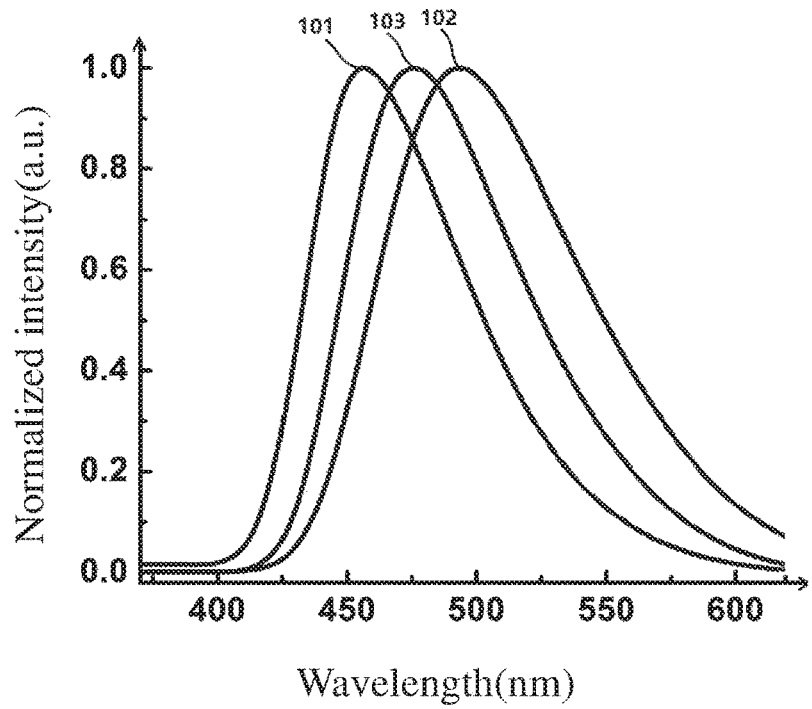
FIG. 2 is a photoluminescence spectrum of a synthesized compound according to an embodiment of the present disclosure in a toluene solution at room temperature.

As shown in FIG. 2, a first curve 101 is a photoluminescence spectrum of the first target compound in a toluene solution at room temperature, and a normalized intensity between the wavelengths of 430 nm and 500 nm is relatively high. The normalized intensity reaches a maximum at a wavelength of 450 nm to 460 nm and has a highest photoluminescence efficiency.

Figure 3:
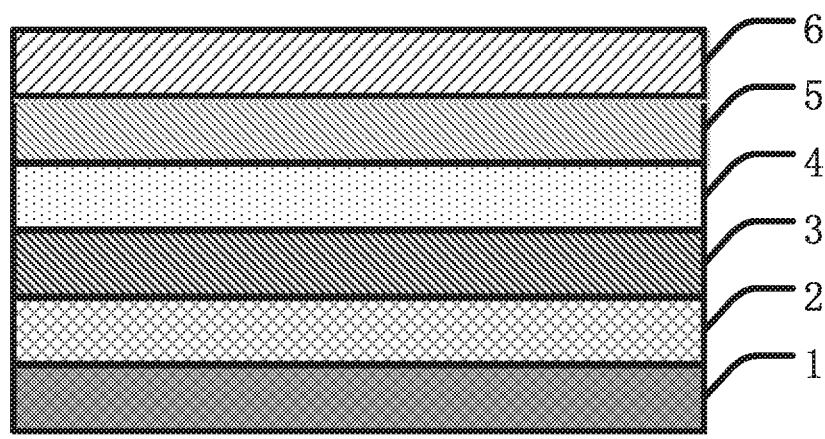
FIG. 3 is a structural schematic diagram of an electroluminescent device according to an embodiment of the present disclosure.

As shown in FIG. 3, the present embodiment further provides an electroluminescent device comprising: a substrate layer 1; a hole injecting layer 2 disposed on an upper surface of the substrate layer 1; and a transporting layer 3 disposed on an upper surface of the hole injecting layer 2; a luminescent layer 4 disposed on an upper surface of the transporting layer 3; an electron transporting layer 5 disposed on an upper surface of the luminescent layer 4; and a cathode layer 6 disposed on an upper surface of the electron transporting layer 5, wherein the luminescent layer 4 is the green light thermally activated delayed fluorescent material, i.e., the first target compound.

Under a high vacuum condition, a layer of 1 nm to 5 nm of molybdenum trioxide ($MoO_3$) is evaporated on a cleaned substrate layer 1 to obtain a hole injecting layer 2, and a material of the substrate layer 1 is glass and conductive glass (ITO). A layer of 20 nm to 50 nm of 4,4',4"-tris(carbazol-9-yl)triphenylamine (TCTA) is evaporated on the hole injecting layer 2 to obtain a transporting layer 3. A layer of 30 nm to 50 nm and 3% of the green light thermally activated delayed fluorescent material and mCBP are evaporated on the transporting layer 3 to obtain a luminescent layer 4. A layer of 1,3,5-tris(3-(3-pyridyl)phenyl)benzene (Tm3PyPB)) of 30 nm to 50 nm is evaporated on the luminescent layer 4 to obtain an electron transporting layer 5. And a under high vacuum condition, a layer of 0 to 5 nm lithium fluoride and 50 nm to 200 nm aluminum are evaporated on the electron transporting layer 5 to obtain a cathode layer 6, so as to finally form a first electroluminescent device.

A current-brightness-voltage characteristic of the device is performed by a Keithley source measurement system (Keithley 2400 Sourcemeter, Keithley 2000 Currentmeter) with a calibrated silicon photodiode. An electroluminescence spectrum is measured by a French JY company SPEX CCD3000 spectrometer. All measurements are done at room temperature in an atmosphere.

Performance parameters of the first electroluminescent device prepared in embodiment 1 are measured below, and the measured performance parameters are shown in Table 2 below.

Table 2 shows measured parameters such as a highest current efficiency and a maximum external quantum efficiency of the first electroluminescent device:

| device | highest current efficiency (cd/A) | CIEy | Maximum external quantum efficiency (%) |
| --- | --- | --- | --- |
| First electroluminescent device | 34.6 | 0.12 | 25.7 |

The electroluminescent device fabricated by green light thermally activated delayed fluorescent material has a relatively high luminous efficiency and brightness, a high production efficiency, and a long service life, so as to fabricate a series of high performance OLEDs.

Embodiment 2

The present embodiment provides a green light thermally activated delayed fluorescent material, which is a target compound reacted and synthesized by an electron donor and an electron acceptor, wherein the target compound is a D-A molecular structure, wherein, in the D-A molecular, the D is the electron donor, the A is the electron acceptor, the electron acceptor has a fluorine-containing group and a bromine-containing group, the electron acceptor is a planar electron acceptor with an ultra-low triplet state energy level, and a triplet state energy level of the target compound ranges from 1.0 to 2.0 eV. In the present embodiment, the electron donor is phenoxazine, and a molecular structure of the electron acceptor is

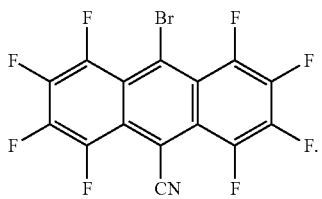 [SMILES: N#Cc1c2c(F)c(F)c(F)c(F)c2c(Br)c2c(F)c(F)c(F)c(F)c12]

A molecular structure of a second target compound synthesized by the electron donor and the electron acceptor is as follows:

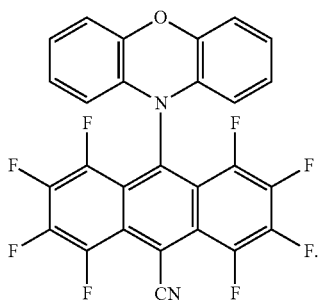 [SMILES: N#Cc1c2c(F)c(F)c(F)c(F)c2c(N2c3ccccc3Oc3ccccc32)c2c(F)c(F)c(F)c(F)c12]

The present embodiment uses a clever molecular design to synthesize a green light thermally activated delayed fluorescent material having a low singlet-triplet state energy level difference, a high luminous efficiency, and a fast reverse crossing enthalpy constant (a constant value ranging from $1*10^4$/s to $1*10^7$/s), and achieve a structure being fine-tuned to cover the spectrum from blue light to green light simultaneously.

As shown in FIG. 1, in order to explain the green light thermally activated delayed fluorescent material of the present disclosure in more detail, the embodiment further provides a synthesizing method of the green light thermally activated delayed fluorescent material, which has a reaction formula substantially as shown in formula (2):

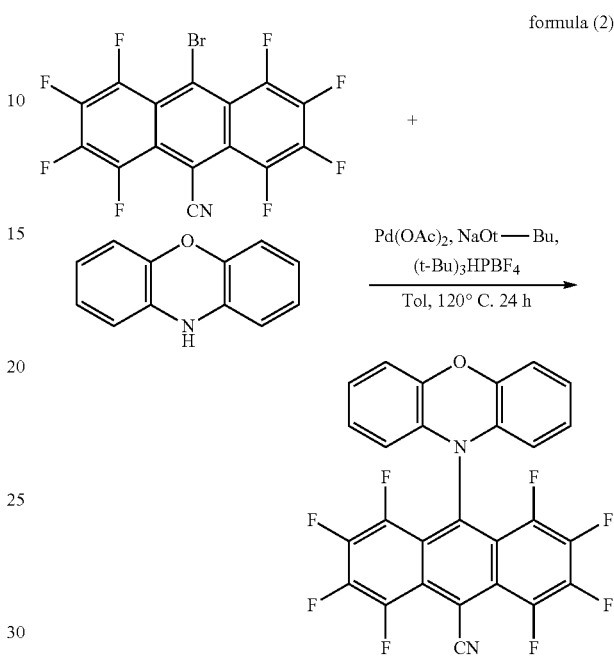

formula (2)

In formula (2), a molar ratio of the electron acceptor to the electron donor is from 1:1 to 1:2.

The synthesizing method of the present embodiment is explained in detail below with reference to formula (2), which includes the following steps:

In a reaction solution preparation step, 2.12 g (5 mmol) of the electron acceptor, 1.1 g (6 mmol) of the electron donor of phenoxazine, a catalyst of 45 mg (0.2 mmol) of palladium acetate, and 0.17 g (0.6 mmol) of tri-tert-butylphosphine tetrafluoroborate are placed in a 100 mL two-necked flask, and 0.58 g (6 mmol) of sodium t-butoxide (NaOt-Bu) is added into the 100 mL two-necked flask in a glove box, the reaction liquid is obtained. Because sodium t-butoxide (NaOt-Bu) reacts easily with water to release hydrogen, it is very dangerous. Therefore, it is stored in the glove box under an argon atmosphere, and it is also used under the argon atmosphere.

In a target compound synthesis step, reaction conditions of the reaction solution are provided. 30 mL to 50 mL of water-and-oxygen removed toluene are added into the glove box to thoroughly react at a temperature of 100° C. to 200° C. to obtain a mixed solution. The mixed solution has a second target compound formed by the reaction.

In an extraction step, the mixed solution is cooled to a room temperature and poured into a 100 mL to 300 mL ice-water mixture. The second target compound in the mixed solution is extracted multiple times with the dichloromethane.

In a target compound purification treatment step, an organic phase is combined, and the first target compound is initially purified by silica gel column chromatography using a developing solvent to obtain a purified product. In the silica gel column chromatography method, the developing agent is dichloromethane and n-hexane, and a volume ratio of the dichloromethane to n-hexane is 3:2. The first target compound is isolated and purified to obtain a green powder of 1.9 g in a yield of 68%.

Parameter analysis of the obtained second target compound is performed by a detecting instrument, and the analysis results include a nuclear magnetic resonance spectrum result, a carbon spectrum result, and a mass spectrometry result. Among them, results of a nuclear magnetic resonance spectrum and a carbon spectrum are $^1$H NMR (300 MHz, $CD_2Cl_2$, δ): 7.14 (t, J=6.3 Hz, 2H), 7.01-6.96 (m, 6H). A mass spectral results is: MS (EI) m/z: [M]+calcd (theoretical value) for $C_{27}H_8F_8N_2O$, 528.05; found (experimental value), 528.01.

The present embodiment synthesizes a green light thermally activated delayed fluorescent material having significant thermal activation delayed fluorescence characteristics by a combination of different functional groups, wherein a synthesizing percentage is high. In the synthesized product, the thermally activated delayed fluorescent material has a high proportion in the entire synthesized product, and its photoluminescence quantum yield is high.

Characteristic parameters of the first target compound are analyzed below, and the analysis results are shown in Table 3 below.

Table 3 shows the measured parameters such as the lowest singlet state (S1) and the lowest triplet state energy level (T1) of the second target compound:

| Compound | PL Peak (nm) | $S_1$ (eV) | $T_1$ (eV) | $\Delta E_{ST}$ (eV) | HOMO (eV) | LUMO (eV) |
|---|---|---|---|---|---|---|
| Second target compound | 481 | 2.58 | 2.49 | 0.09 | −5.63 | −2.44 |

As shown in FIG. 2, a second curve 102 is a photoluminescence spectrum of the second target compound in a toluene solution at room temperature, and a normalized intensity between the wavelengths of 460 nm and 550 nm is relatively high. The normalized intensity reaches a maximum at a wavelength of 500 nm and has a highest photoluminescence efficiency.

As shown in FIG. 3, the present embodiment further provides an electroluminescent device comprising: a substrate layer 1; a hole injecting layer 2 disposed on an upper surface of the substrate layer 1; and a transporting layer 3 disposed on an upper surface of the hole injecting layer 2; a luminescent layer 4 disposed on an upper surface of the transporting layer 3; an electron transporting layer 5 disposed on an upper surface of the luminescent layer 4; and a cathode layer 6 disposed on an upper surface of the electron transporting layer 5, wherein the luminescent layer 4 is the green light thermally activated delayed fluorescent material, i.e., the second target compound.

Under a high vacuum condition, a layer of 1 nm to 5 nm of molybdenum trioxide ($MoO_3$) is evaporated on a cleaned substrate layer 1 to obtain a hole injecting layer 2, and a material of the substrate layer 1 is glass and conductive glass (ITO). A layer of 20 nm to 50 nm of 4,4',4"-tris(carbazol-9-yl)triphenylamine (TCTA) is evaporated on the hole injecting layer 2 to obtain a transporting layer 3. A layer of 30 nm to 50 nm and 3% of the green light thermally activated delayed fluorescent material and mCBP are evaporated on the transporting layer 3 to obtain a luminescent layer 4. A layer of 1,3,5-tris(3-(3-pyridyl)phenyl)benzene (Tm3PyPB) of 30 nm to 50 nm is evaporated on the luminescent layer 4 to obtain an electron transporting layer 5. And a under high vacuum condition, a layer of 0 to 5 nm lithium fluoride and 50 nm to 200 nm aluminum are evaporated on the electron transporting layer 5 to obtain a cathode layer 6, so as to finally form a second electroluminescent device.

A current-brightness-voltage characteristic of the device is performed by a Keithley source measurement system (Keithley 2400 Sourcemeter, Keithley 2000 Currentmeter) with a calibrated silicon photodiode. An electroluminescence spectrum is measured by a French JY company SPEX CCD3000 spectrometer. All measurements are done at room temperature in an atmosphere.

Performance parameters of the second electroluminescent device prepared in embodiment 2 are measured below, and the measured performance parameters are shown in Table 4 below.

Table 4 shows measured parameters such as a highest current efficiency and a maximum external quantum efficiency of the second electroluminescent device:

| device | highest current efficiency (cd/A) | CIEy | Maximum external quantum efficiency (%) |
|---|---|---|---|
| Second electroluminescent device | 100.1 | 0.68 | 33.8 |

The electroluminescent device fabricated by green light thermally activated delayed fluorescent material has a relatively high luminous efficiency and brightness, a high production efficiency, and a long service life, so as to fabricate a series of high performance OLEDs.

Embodiment 3

The present embodiment provides a green light thermally activated delayed fluorescent material, which is a target compound reacted and synthesized by an electron donor and an electron acceptor, wherein the target compound is a D-A molecular structure, wherein, in the D-A molecular, the D is the electron donor, the A is the electron acceptor, the electron acceptor has a fluorine-containing group and a bromine-containing group, the electron acceptor is a planar electron acceptor with an ultra-low triplet state energy level, and a triplet state energy level of the target compound ranges from 1.0 to 2.0 eV. In the present embodiment, the electron donor is phenoxazine, and a molecular structure of the electron acceptor is

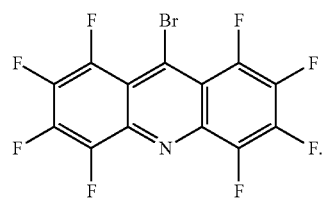 [SMILES: Fc1c(F)c(F)c2c(Br)c3c(F)c(F)c(F)c(F)c3nc2c1F]

A molecular structure of a third target compound synthesized by the electron donor and the electron acceptor is as follows:

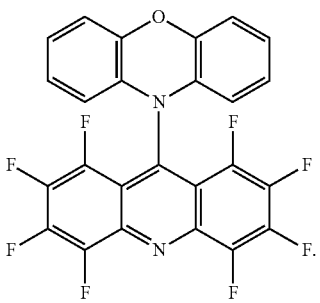 [SMILES: Fc1c(F)c(F)c2c(N3c4ccccc4Oc4ccccc43)c3c(F)c(F)c(F)c(F)c3nc2c1F]

The present embodiment uses a clever molecular design to synthesize a green light thermally activated delayed fluorescent material having a low singlet-triplet state energy level difference, a high luminous efficiency, and a fast reverse crossing enthalpy constant (a constant value ranging from $1*10^4$/s to $1*10^7$/s), and achieve a structure being fine-tuned to cover the spectrum from blue light to green light simultaneously.

As shown in FIG. 1, in order to explain the green light thermally activated delayed fluorescent material of the present disclosure in more detail, the embodiment further provides a synthesizing method of the green light thermally activated delayed fluorescent material, which has a reaction formula substantially as shown in formula (3):

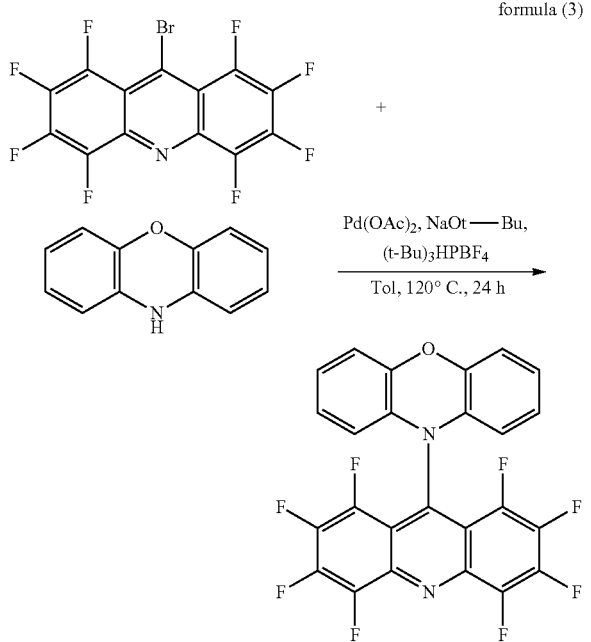

formula (3)

In formula (3), a molar ratio of the electron acceptor to the electron donor is from 1:1 to 1:1.5.

The synthesizing method of the present embodiment is explained in detail below with reference to formula (3), which includes the following steps:

In a reaction solution preparation step, 2.02 g (5 mmol) of the electron acceptor, 1.1 g (6 mmol) of the electron donor of phenoxazine, a catalyst of 45 mg (0.2 mmol) of palladium acetate, and 0.17 g (0.6 mmol) of tri-tert-butylphosphine tetrafluoroborate are placed in a 100 mL two-necked flask, and 0.58 g (6 mmol) of sodium t-butoxide (NaOt-Bu) is added into the 100 mL two-necked flask in a glove box, the reaction liquid is obtained. Because sodium t-butoxide (NaOt-Bu) reacts easily with water to release hydrogen, it is very dangerous. Therefore, it is stored in the glove box under an argon atmosphere, and it is also used under the argon atmosphere.

In a target compound synthesis step, reaction conditions of the reaction solution are provided. 30 mL to 50 mL of water-and-oxygen removed toluene are added into the glove box to thoroughly react at a temperature of 100° C. to 200° C. to obtain a mixed solution. The mixed solution has a third target compound formed by the reaction.

In an extraction step, the mixed solution is cooled to a room temperature and poured into a 100 mL to 300 mL ice-water mixture. The third target compound in the mixed solution is extracted multiple times with the dichloromethane.

In a target compound purification treatment step, an organic phase is combined, and the third target compound is initially purified by silica gel column chromatography using a developing solvent to obtain a purified product. In the silica gel column chromatography method, the developing agent is dichloromethane and n-hexane, and a volume ratio of the dichloromethane to n-hexane is 3:2. The third target compound is isolated and purified to obtain a green powder of 1.8 g in a yield of 71%.

Parameter analysis of the obtained second target compound is performed by a detecting instrument, and the analysis results include a nuclear magnetic resonance spectrum result, a carbon spectrum result, and a mass spectrometry result. Among them, results of a nuclear magnetic resonance spectrum and a carbon spectrum are $^1$H NMR (300 MHz, $CD_2Cl_2$, δ): 7.14 (t, J=6.3 Hz, 2H), 7.01-6.96 (m, 6H). A mass spectral results is: MS (EI) m/z: [M]+calcd (theoretical value) for $C_{25}H_8F_8N_2O$, 504.05; found (experimental value), 504.00.

The present embodiment synthesizes a green light thermally activated delayed fluorescent material having significant thermal activation delayed fluorescence characteristics by a combination of different functional groups, wherein a synthesizing percentage is high. In the synthesized product, the thermally activated delayed fluorescent material has a high proportion in the entire synthesized product, and its photoluminescence quantum yield is high.

Characteristic parameters of the third target compound are analyzed below, and the analysis results are shown in Table 5 below.

Table 5 shows the measured parameters such as the lowest singlet state (S1) and the lowest triplet state energy level (T1) of the third target compound:

| Compound | PL Peak (nm) | $S_1$ (eV) | $T_1$ (eV) | $\Delta E_{ST}$ (eV) | HOMO (eV) | LUMO (eV) |
|---|---|---|---|---|---|---|
| Third target compound | 500 | 2.48 | 2.40 | 0.08 | −5.66 | −2.43 |

As shown in FIG. 2, a third curve 103 is a photoluminescence spectrum of the third target compound in a toluene solution at room temperature, and a normalized intensity between the wavelengths of 450 nm and 575 nm is relatively high. The normalized intensity reaches a maximum at a wavelength of 475 nm and has a highest photoluminescence efficiency.

As shown in FIG. 3, the present embodiment further provides an electroluminescent device comprising: a substrate layer 1; a hole injecting layer 2 disposed on an upper surface of the substrate layer 1; and a transporting layer 3 disposed on an upper surface of the hole injecting layer 2; a luminescent layer 4 disposed on an upper surface of the transporting layer 3; an electron transporting layer 5 disposed on an upper surface of the luminescent layer 4; and a cathode layer 6 disposed on an upper surface of the electron transporting layer 5, wherein the luminescent layer 4 is the green light thermally activated delayed fluorescent material, i.e., the third target compound.

Under a high vacuum condition, a layer of 1 nm to 5 nm of molybdenum trioxide (MoO₃) is evaporated on a cleaned substrate layer 1 to obtain a hole injecting layer 2, and a material of the substrate layer 1 is glass and conductive glass (ITO). A layer of 20 nm to 50 nm of 4,4',4''-tris(carbazol-9-yl)triphenylamine (TCTA) is evaporated on the hole injecting layer 2 to obtain a transporting layer 3. A layer of 30 nm to 50 nm and 3% of the green light thermally activated delayed fluorescent material and mCBP are evaporated on the transporting layer 3 to obtain a luminescent layer 4. A layer of 1,3,5-tris(3-(3-pyridyl)phenyl)benzene (Tm3PyPB)) of 30 nm to 50 nm is evaporated on the luminescent layer 4 to obtain an electron transporting layer 5. And a under high vacuum condition, a layer of 0 to 5 nm lithium fluoride and 50 nm to 200 nm aluminum are evaporated on the electron transporting layer 5 to obtain a cathode layer 6, so as to finally form a third electroluminescent device.

A current-brightness-voltage characteristic of the device is performed by a Keithley source measurement system (Keithley 2400 Sourcemeter, Keithley 2000 Currentmeter) with a calibrated silicon photodiode. An electroluminescence spectrum is measured by a French JY company SPEX CCD3000 spectrometer. All measurements are done at room temperature in an atmosphere.

Performance parameters of the third electroluminescent device prepared in embodiment 3 are measured below, and the measured performance parameters are shown in Table 6 below.

Table 6 shows measured parameters such as a highest current efficiency and a maximum external quantum efficiency of the third electroluminescent device:

| device | highest current efficiency (cd/A) | CIEy | Maximum external quantum efficiency (%) |
|---|---|---|---|
| Third electroluminescent device | 115.5 | 0.70 | 36.5 |

The electroluminescent device fabricated by green light thermally activated delayed fluorescent material has a relatively high luminous efficiency and brightness, a high production efficiency, and a long service life, so as to fabricate a series of high performance OLEDs.

The description above is merely preferred embodiments of the present disclosure. It is noted that, for one skilled in the art, many changes and modifications to the described embodiment can be carried out without departing from the principles of the disclosure and these changes and modifications should also be considered as protection scope of the present disclosure.

What is claimed is:

1. A green light thermally activated delayed fluorescent material, which is a target compound reacted and synthesized by an electron donor and an electron acceptor, wherein the target compound is a D-A molecular structure, wherein, in the D-A molecular, the D is the electron donor, the A is the electron acceptor, the electron acceptor has a fluorine-containing group and a bromine-containing group, the electron acceptor is a planar electron acceptor with an ultra-low triplet state energy level, and a triplet state energy level of the target compound ranges from 1.0 to 2.0 eV, wherein the electron donor is phenoxazine, and a molecular structure of the electron acceptor is

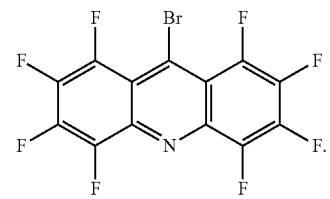 [SMILES: Fc1c(F)c(F)c2c(Br)c3c(F)c(F)c(F)c(F)c3nc2c1F]

2. The green light thermally activated delayed fluorescent material according to claim 1, wherein the D-A molecular structure of the green light thermally activated delayed fluorescent material is one of

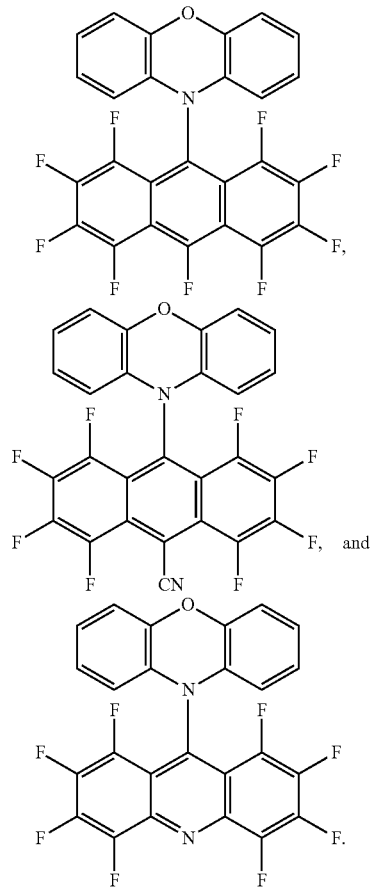

3. A synthesizing method of a green light thermally activated delayed fluorescent material, comprising:
a reaction solution preparation step of placing an electron donor, an electron acceptor, and a catalyst into a reaction vessel to obtain a reaction solution;
a target compound synthesis step of placing the reaction solution at a temperature from 110° C. to 130° C. to thoroughly react and thus obtain a mixed solution, wherein the mixed solution has a target compound formed after reacting;

an extraction step of cooling the mixed solution to a room temperature to extract the target compound from the mixed solution; and a target compound purification treatment step of separating and purifying the target compound to obtain the green thermally activated delayed fluorescent material, wherein the electron donor is phenoxazine, and a molecular structure of the electron acceptor is

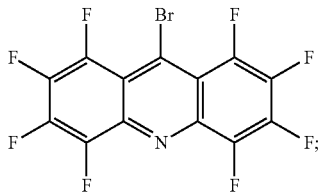

and
the catalyst includes palladium acetate, tri-tert-butylphosphine tetrafluoroborate, and sodium t-butoxide.

4. The synthesizing method of the green light thermally activated delayed fluorescent material according to claim 3, wherein in the reaction solution preparation step, a molar ratio of the electron acceptor to the electron donor is from 1:1 to 1:3.

5. The synthesizing method of the green light thermally activated delayed fluorescent material according to claim 3, wherein in the reaction solution preparation step, the palladium acetate and the tri-tert-butylphosphine tetrafluoroborate together with the electron donor and the electron acceptor are firstly placed into the reaction vessel, the reaction vessel is further placed under an argon gas environment, and the sodium t-butoxide and toluene which removes water and oxygen are added into the reaction vessel, so as to obtain the reaction solution.

6. The synthesizing method of the green light thermally activated delayed fluorescent material according to claim 3, wherein the extraction step comprises:

pouring the reaction solution into an ice water mixture, and performing multiple extractions using dichloromethane; and after the multiple extractions, combining organic phases to obtain the target compound.

7. The synthesizing method of the green light thermally activated delayed fluorescent material according to claim 3, wherein a step of purifying the target compound comprises:

purifying the target compound by a silica gel column chromatography using a developing solvent to obtain a purified product, wherein the developing agent in the silica gel column chromatography method is dichloromethane and n-hexane, and a volume ratio of the dichloromethane to the n-hexane is 3:2.

8. An electroluminescent device, comprising:

a substrate layer;

a hole injecting layer disposed on a side surface of the substrate layer;

a transporting layer disposed on a side surface of the hole injecting layer away from the substrate layer;

a luminescent layer disposed on a side surface of the transporting layer away from the hole injecting layer;

an electron transporting layer disposed on a side surface of the luminescent layer away from the transporting layer; and a cathode layer disposed on a side surface of the electron transporting layer away from the luminescent layer;

wherein a material of the luminescent layer is a green light thermally activated delayed fluorescent material, wherein the green light thermally activated delayed fluorescent material is a target compound reacted and synthesized by an electron donor and an electron acceptor, wherein the target compound is a D-A molecular structure, wherein, in the D-A molecular, the D is the electron donor, the A is the electron acceptor, the electron acceptor has a fluorine-containing group and a bromine-containing group, the electron acceptor is a planar electron acceptor with an ultra-low triplet state energy level, and a triplet state energy level of the target compound ranges from 1.0 to 2.0 eV, wherein the electron donor is phenoxazine, and a molecular structure of the electron acceptor is

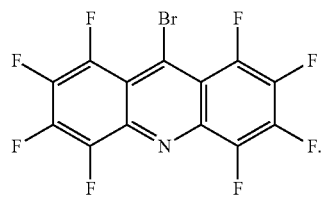 [SMILES: Fc1c(F)c(F)c2c(Br)c3c(F)c(F)c(F)c(F)c3nc2c1F]

* * * * *